(12) United States Patent
Hanrahan et al.

(10) Patent No.: US 12,142,354 B2
(45) Date of Patent: Nov. 12, 2024

(54) SYSTEMS AND METHODS OF MEDICAL DEVICE DATA COLLECTION AND PROCESSING

(71) Applicant: General Electric Company, Wauwatosa, WI (US)

(72) Inventors: James Joseph Hanrahan, Madison, WI (US); Guy Vesto, Barrington, IL (US)

(73) Assignee: General Electric Company, Schenectady, NY (US)

(*) Notice: Subject to any disclaimer, the term of this patent is extended or adjusted under 35 U.S.C. 154(b) by 733 days.

(21) Appl. No.: 17/140,959

(22) Filed: Jan. 4, 2021

(65) Prior Publication Data

US 2021/0125694 A1   Apr. 29, 2021

Related U.S. Application Data

(63) Continuation of application No. 15/273,103, filed on Sep. 22, 2016, now abandoned.

(51) Int. Cl.
*G16H 10/60* (2018.01)
*G06F 16/2455* (2019.01)
(Continued)

(52) U.S. Cl.
CPC ....... *G16H 10/60* (2018.01); *G06F 16/24568* (2019.01); *G16H 40/20* (2018.01);
(Continued)

(58) Field of Classification Search
CPC ........ G16H 80/00; G16H 40/67; G16H 20/17; G16H 40/63; G16H 40/40; G16H 20/10;
(Continued)

(56) References Cited

U.S. PATENT DOCUMENTS

2002/0156352 A1* 10/2002 Eggers ................... G16H 40/63
  600/300
2009/0240526 A1* 9/2009 Vesto ..................... G16H 50/20
  705/3
(Continued)

OTHER PUBLICATIONS

R. Kamaleswaran, C. McGregor and J. M. Eklund, "A method for clinical and physiological event stream processing," 2010 Annual International Conference of the IEEE Engineering in Medicine and Biology, Buenos Aires, Argentina, 2010, pp. 1170-1173, doi: 10.1109/IEMBS.2010.5626243 (Year: 2010).*

*Primary Examiner* — Joseph D Burgess

(57) ABSTRACT

A system for processing medical device data can include a processor to receive a plurality of streaming time series of medical device data from medical devices, wherein the medical device data comprises machine data. The processor can also apply a plurality of case identification rules to the plurality of streaming time series of medical device data to identify portions of the plurality of streaming time series of medical device data representing clinical cases. The processor can also execute streaming analytics to apply a plurality of event detection rules to the portions of the plurality streaming time series of medical device data to identify events within each identified clinical case. The processor can generate one or more groups for the identified events based upon predefined recipients of notifications for the identified events and transmit event notifications for each of the identified events to the predefined recipients.

20 Claims, 7 Drawing Sheets

(51) Int. Cl.
*G16H 40/20* (2018.01)
*G16H 40/63* (2018.01)
*G16H 40/67* (2018.01)
*G16H 50/20* (2018.01)
*H04L 65/75* (2022.01)

(52) U.S. Cl.
CPC .............. *G16H 40/63* (2018.01); *G16H 40/67* (2018.01); *G16H 50/20* (2018.01); *H04L 65/762* (2022.05)

(58) Field of Classification Search
CPC ........ G16H 40/20; G16H 10/60; G16H 20/40; G16H 50/30; G16H 15/00; G16H 40/60; G16H 50/70; G16H 70/40; G06Q 10/10
See application file for complete search history.

(56) References Cited

U.S. PATENT DOCUMENTS

| | | | | |
|---|---|---|---|---|
| 2010/0223073 | A1* | 9/2010 | Nearman | G16H 40/67 380/255 |
| 2015/0351695 | A1* | 12/2015 | Cronin | A61B 5/7475 600/300 |
| 2022/0020491 | A1* | 1/2022 | Martin | G16H 15/00 |

* cited by examiner

Carestation™ Insights

Agent Cost Dashboard — Monthly Overview

Monthly Averages
- Induction Cost per case: $9.60 / 5.8 L/min
- Maintenance Cost per Min: $0.16 / 1.8 L/min

Monthly Totals
- # of Machines: 6
- # of Cases: 374
- Total Cost: $3,589

Average Agent Consumption
- Sevoflurane: 19.8 mL/case — $0.13 cost/min
- Desflurane: 20.8 mL/case — $0.21 cost/min
- Isoflurane: 0.0 mL/case — $0.00 cost/min

Monthly Totals to Date — Daily Trend

| Info | Total | vs. Prev.Mo. |
|---|---|---|
| Cases | 374 | ▲10% |
| AA | 7526 mL | ▽9% |
| Sevo | 5009 mL | -0% |
| Des | 2516 mL | ▲6% |
| Iso | 0 mL | -0% |
| Cost | $3,589 | ▽15% |

Date | Month | ← 06/2016 → | Agent Cost | Checkout

Monthly View — June 2016

| OR | Device ID# | Cases | mL of SEV | mL of DES | mL of ISO | Cost | Ave Ind L/Min | Ave Main L/Min | Action |
|---|---|---|---|---|---|---|---|---|---|
| OR1 | OR1 | 63 | 772.2 | 499.2 | 0.0 | $623.38 | 6.0 | 1.6 | View Details |
| OR2 | OR2 | 62 | 871.2 | 374.4 | 0.0 | $584.35 | 5.9 | 2.0 | View Details |
| OR3 | OR3 | 59 | 752.4 | 436.8 | 0.0 | $576.14 | 5.8 | 1.8 | View Details |
| OR4 | OR4 | 65 | 910.8 | 395.2 | 0.0 | $613.30 | 6.0 | 1.9 | View Details |
| OR5 | OR5 | 63 | 891.0 | 374.4 | 0.0 | $592.27 | 5.9 | 2.1 | View Details |
| OR6 | OR6 | 62 | 811.8 | 436.8 | 0.0 | $599.90 | 6.0 | 1.7 | View Details |

FIG. 4

Checkout Dashboard

| OR | Device ID# | Vent and Gas | Circuit Leak | Low P Leak | Agent Delivery | Last Device Activity |
|----|-----------|--------------|--------------|------------|----------------|---------------------|
| OR1 | OR1 | ○ | ○ | ○ | ○ | 06/21/2016 16:28 |
| OR2 | OR2 | ①  | ①  | ①  | ①  | 06/21/2016 16:28 |
| OR3 | OR3 | ○ | ○ | ○ | ○ | 06/21/2016 16:28 |
| OR4 | OR4 | ○ | ○ | ○ | ○ | 06/21/2016 16:28 |
| OR5 | OR5 | ○ | ○ | ○ | ○ | 06/21/2016 16:28 |
| OR6 | OR6 | ○ | ○ | ○ | ○ | 06/21/2016 16:28 |

LEGEND

○ Indicates test has been completed today

③ Number inside a circle indicates how many Calendar days since last test was completed (for example, this means it has been 3 days since test was run).

FIG. 5

SYSTEMS AND METHODS OF MEDICAL DEVICE DATA COLLECTION AND PROCESSING

CROSS-REFERENCE TO RELATED APPLICATIONS

The present application is a continuation of U.S. patent application Ser. No. 15/273,103, filed on Sep. 22, 2016 and titled "SYSTEMS AND METHODS OF MEDICAL DEVICE DATA COLLECTION AND PROCESSING," the contents of which are incorporated herein by reference in their entirety.

BACKGROUND

The present disclosure is related to the field of data processing and analytics. More specifically, the present disclosure is related to the collection and processing of medical device data from a plurality of medical devices.

Medical devices generate large amounts of data from sensors and inputs that are used in real-time on the device to display relevant information or to provide alerts to users of the device. In some settings, this data is made available to external systems through proprietary or standards-based data messaging. Examples of these systems include hospital information systems (HIS) and/or electronic health records (EHR). HIS and EHR systems collect and process a variety of information, including patient data. HIS systems seek to coordinate the administrative, financial, legal needs of a hospital system, which may include the management of patient data or particular departments within a hospital system or network, for example laboratory services and patient imaging. EHR systems seek to collect and coordinate health information generated both on a patient by patient basis as well as population information. In either case of HIS or EHR systems, these currently available systems only connect to medical devices in a limited manner and to the extent that information directly from medical devices is incorporated into these systems, such information is typically the physiological data directly acquired from such medical devices, e.g. heart rate, pulse rate, blood oxygenation, blood pressure, temperature, respiration rate, etc.

However, medical devices as typically used in hospitals produce significantly more data than merely the monitor physiological parameters of a patient. Therefore, new systems and methods are desirable to collect and process this medical device data and to incorporate information gained from these systems into hospital system workflows and decision making.

BRIEF DISCLOSURE

An example embodiment of a method of medical device data processing includes receiving streaming time series medical device data from a plurality of medical devices. All of the streaming time series medical device data is stored in a data lake which comprises at least one computer memory. Streaming analytics are conducted to apply a plurality of case identification rules to the streaming time series medical device data to identify clinical cases in the streaming time series medical device data. Upon identification of a clinical case in the streaming time series medical data, the identified clinical case is stored in a computer memory. Streaming analytics are conducted to apply a plurality of event detection rules to the streaming time series medical device data to identify events in the streaming time series medical device data. The identified events are routed to an event notifier. The identified events are grouped in the event notifier into notification groups. Event notifications are transmitted for each of the identified events to recipient across communication platforms associated with each of the notification groups.

An example embodiment of a system for processing medical device data from the system includes a data ingestion module that receives streaming time series medical device data and preprocesses the streaming time series medical device data. The received streaming time series medical device data is stored in at least one computer memory comprising a data lake. A streaming analytics module receives the streaming time series medical device data and applies a plurality of event detection rules to the streaming time series medical device data to identify events in the streaming time series medical device data to identify events in the streaming time series medical device data. An event notifier receives the identified events in the streaming time series medical device data. The event notifier groups the identified events based upon predefined recipients of notifications for the identified events. The event notifier transmits event notifications for each of the identified events to the predefined recipients associated with each of the groups across at least one communication platform associated with each of the groups.

BRIEF DESCRIPTION OF THE DRAWINGS

FIG. 4 depicts an exemplary embodiment of an agent cost dashboard.

FIG. 5 depicts an exemplary embodiment of a checkout dashboard.

DETAILED DISCLOSURE

Embodiments of systems and methods as disclosed herein operate to collect and process a wide variety of medical device data. Medical device data includes physiological data that is acquired from a patient by a medical device and machine data collected internally from the medical device itself. Machine data can include alarms, device status, settings, messages, and measured operational data. Machine data may further includes settings and values that represent specific actions taken with the medical device for example, in response to automated controls or due to clinician inputs. For example, in an anesthesia delivery machine, this may include changes to oxygen and/or anesthetic agent concentrations. The machine data may further include clinical and/or technical alarms initiated by the medical device or device diagnostic information. Still further examples of the machine data include proactive or predictive service alerts from the medical device, maintenance checkout information and/or processor clock cycle signals or power signals or other operational signals from various components of the medical device indicative that the medical device is turned on, in use, in operation, held in a stand by condition, or turned off.

This machine data can be collected in time series format as provided from the medical devices themselves. As used herein, the time series format of the medical device data can include waveforms, binary data, numeric data, and/or textual data in a time series format. Embodiments of the systems and methods as disclosed herein receive the medical device data from the medical devices at a frequency similar to the frequency at which it is produced by the medical device. In embodiments, this increased velocity of the received data and the monitoring and analysis of medical device machine data can enable improved monitoring systems and method as disclosed herein. As described in further detail herein embodiments of systems and methods support high speed data ingestion, enrichment, normalization, and data curation of the medical device data. The medical device data can undergo real time analysis and further enrichment of the data with event detection and notation. While all of the medical device data can be saved for retrospective and automated machine learning and analysis, event detection and notation can be used to create further exemplary files of medical device data stemming from particular events or conditions which can be used as exemplary or case study data for further analysis.

In embodiments, machine learning and data analysis of the collected medical device data can be used to develop and refine control, early detection/predictive, and/or alarm algorithms to improve clinician use of the medical devices, hospital workflow, operation or alarm settings of the medical devices themselves, or event detection within the system.

Figure 1:
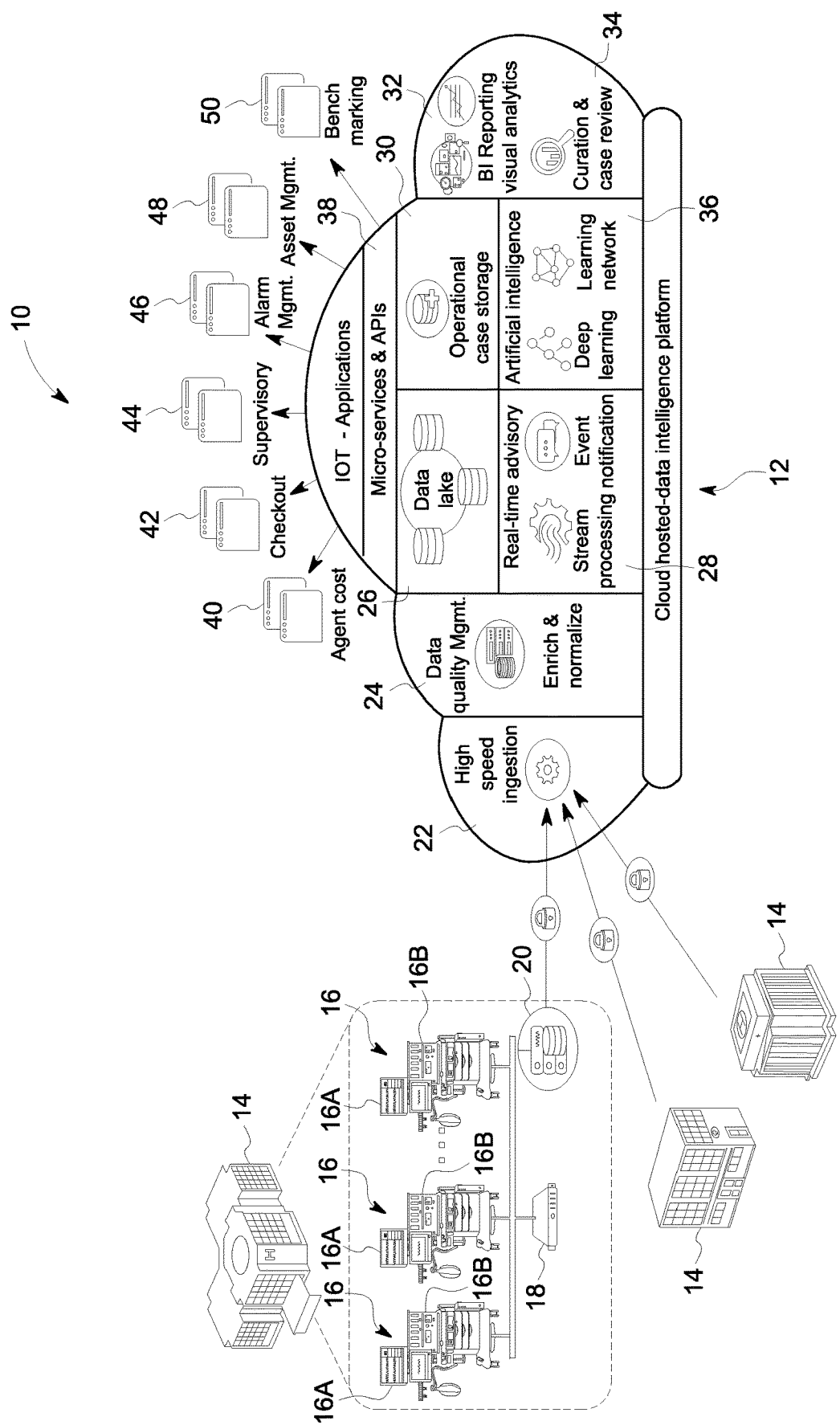
FIG. 1 is a system diagram of an exemplary embodiment of a system for medical device data collection and processing.

FIG. 1 depicts an exemplary embodiment of a system 10 for medical device data collection and processing. The system 10 includes a medical device data (MDD) processing system 12. The MDD processing system 12 can be implemented in a variety of hardware and/or software implementations, it should be noted that such implementations are not considered to be limiting. For example, it is contemplated that any or all of the MDD processing system 12 may be embodied exclusively in hardware, exclusively in software, exclusively in firmware or in any combination of hardware, software, and/or firmware. Currently, while the following describes exemplary methods and systems the examples provided herein are not the only way to implement such methods and systems.

In embodiments wherein any of the claims are read to cover an entirely software and/or firmware implementation, in any embodiment, at least one of the elements is hereby expressly defined to include a tangible computer readable medium. As used herein, the term tangible computer readable medium is expressly defined to include any type of computer readable storage and to exclude propagating signals. Additionally or alternatively, the example methods and systems may be implemented using coded instruction (e.g., computer readable instructions) stored on a non-transitory computer readable medium such as a flash memory, a read-only memory (ROM) a random-access memory (RAM), a cache, or any other storage media in which information is stored for any duration (e.g. for extended period time periods, permanently, brief instances, for temporarily buffering, and/or for caching of the information). As used herein, the term non-transitory computer readable medium is expressly defined to include any type of computer readable medium and to exclude propagating signals.

In exemplary and non-limiting embodiments of the medical device data processing system 12, the system 12 is implemented by one or more networked processors or computing devices. Processing system 12 may be implemented in a cloud computing platform and/or infrastructure. Memory and processors as referred to herein can be stand alone or integrally constructed as part of various programmable devices, including for example, computers or servers. Computer memory of computer readable storage mediums as referenced herein may include volatile and non-volatile or removable and non-removable media for a storage of electronic-formatted information such as computer readable program instructions or modules of computer readable program instructions, data, etc. that may be stand-alone or as part of a computing device. Examples of computer memory may include, but are not limited to RAM, ROM, EEPROM, flash memory, CD-ROM, DVD-ROM or other optical storage, magnetic cassettes, magnetic tape, magnetic disc, or other magnetic storage devices, or any other medium which can be used to store the desired electronic format of information and which can be accessed by the processor or processors or at least a portion of a computing device.

The MDD processing system 12 is communicatively connected to at least one hospital network 14. Such communicative connections as well as the hospital network itself may include, but are not limited to, a wide area network (WAN); a local area network (LAN); the internet; wired or wireless (e.g. optical, Bluetooth, radio frequency (RF) network; a cloud-based computer infrastructure of computers, routers, servers, gateways, etc.; or any combination thereof associated therewith that allows the system or portions thereof to communicate with one or more computing devices.

The hospital network 14 may exemplarily be a network associated with a portion of a hospital, for example a surgery unit or department of a hospital, or may be more broadly located across medical devices of an entire hospital. It further will be recognized that while some embodiments and implementations of the systems and methods as disclosed herein may seek to operate on a single hospital or unit of a hospital, still other embodiments may connect a plurality of hospital networks, including hospitals currently owned or operated or otherwise affiliated with one another. In still further embodiments while individual hospitals or groups of hospitals may use the MDD processing system 12, the MDD processing system 12 receives and processes information from a plurality of hospital networks including those unaffiliated with one another at the same time.

As depicted in FIG. 1, the hospital network 14 includes a plurality of medical devices 16. The medical devices 16 exemplarily include physiological monitoring devices 16a as well as patient therapy devices 16b. Physiological monitoring devices 16a may include, but are not limited to heart rate monitors, blood pressure oxygenation monitors, respiration monitors, ECG, EEG, or EMG. An exemplary embodiment of an anesthesia delivery machine will be used for discussion purposes as the medical device, and more specifically as the patient therapy device 16b, although it will be recognized by a person of ordinary skill in the art that other devices, including, but not limited to patient respiratory assistance devices or dialysis machines may be further non-limiting examples of patient therapy devices. However, it will be recognized that therapy devices may also include capabilities to not only deliver patient therapy, but also to measure physiological parameters of a patient. For example, embodiments of anesthesia delivery machines may include gas analysis modules operable to measure gas concentrations expired by the patient. In other exemplary embodiments, imaging devices, including, but not limited to X-ray, CT, MRI, and ultrasound devices may be examples of medical devices 16 as contemplated within the present disclosure. Still further examples of medical devices may include video and/or audio recording devices.

In an exemplary embodiment, a limited version of the MDD processing system 12 as described herein may be implemented locally, exemplarily as an anesthesia delivery management system 18. In such an embodiment, the anesthesia delivery management system 18 may operate to collect medical device data from a plurality of anesthesia delivery machines 16b for example, among other things as described herein, to monitor anesthesia agent use between anesthesia delivery machines and across procedures performed by those machines in an effort to visualize anesthetic agent consumption and use as well as to quantify, monitor, and evaluate trends across all of the anesthesia delivery machines in the hospital or surgical unit. In still further embodiments as disclosed herein, the medical device data can be used to manage the schedule and/or maintenance of medical devices used in the hospital or surgical unit.

The medical devices 16 are communicatively connected to one or more gateway devices 20. Gateway devices 20 may exemplarily be edge processing devices, cloud processing devices or internet gateways. The gateway 20 may exemplarily be an internet of things (IOT) gateway which facilitates a secure communications link between the medical devices 16 at the hospital network 14 with the servers, processors, and computer readable media implementing the MDD processing system 12. In exemplary embodiments, the gateway 20 may communicate directly with one or more of the medical devices 16, or may communicate with the medical devices 16 through an intermediate network, for example, the anesthesia delivery management system 18 or another medical device data system or network.

The gateway 20 receives the medical device data as time series data for any of the medical device data available from the medical devices. Exemplary embodiments as described herein will focus on machine data, except where specifically noted, although it will be recognized that other forms of medical device data may be used in similar manners as disclosed with respect to these exemplary embodiments. As noted above, the data streams of machine data are available in time series format as acquired from the medical devices and may include, but are not limited to time series information of alarms, device status, device settings, messages, and measured data. In embodiments, the medical devices may be equipped with sensors that improve the self-awareness of the medical device, e.g. sensors that monitor the function, inputs and/or outputs of various components of the medical device itself. Many such sensors are already incorporated into medical deices such as to measure compressor speeds and/or cycle times, internal pressures, voltages, clock speeds, or temperatures, or other sensors as will be recognized by a person of ordinary skill in the art or as disclosed in further detail herein.

The gateway 20 encrypts the time series formatted data and the encrypted data is transmitted using known wire and/or wireless communication techniques for encrypted data to the server, processors, and data storage carrying out the medical device data processing system 12. The gateway 20 continuously transmits de-identified medical device machine data in time series format over an encrypted communication channel to a high speed data ingestion module 22 of the MDD processing system 12. While the exemplary embodiment described herein may reference de-identified data, it will be recognized that other embodiments may use patient-identified data with appropriate considerations taken for handling patent data. The high speed data ingestion module 22 takes in the real time streams of medical device data. The data ingestion can be performed automatedly and preprocess the received streams of real time data in the time series for later processing by the MDD processing system 12. The high speed ingestion module 22 can receive concurrent data streams from multiple connected devices across multiple sites at a high incoming velocity, for example at or near the frequency at which medical devices can output machine data. In exemplary embodiments the high speed ingestion module 22 is scalable to continue to ingest increased bandwidth of medical device data without significant decrease in ingestion speeds.

The high speed ingestion module 22 takes the time series medical device data from the medical devices of one or more hospital networks and formats it for further processing by a data quality management module 24. In exemplary and non-limiting embodiments, the high speed injection module 22 supports open standard such as ASTMF 2761 or integrated clinical environmental (ICE). The data quality management module normalizes, enriches, and tags the data streams without negatively impacting data latency. In a healthcare environment, a variety of healthcare information products and/or systems may be used to provide medical services, collect medical data, conduct medical exams, etc. Such products and/or systems include the Centricity® suite of products and/or systems as offered by GE Healthcare®. However, many healthcare information systems operate using various messaging standards (e.g., Health Level 7 International (HL7 V2.x/v3), Clinical Document Architecture/Continuity Of Care Document (CDA/CCD), American Society for Testing Materials (ASTM), Digital Imaging and Communications in Medicine (DICOM), etc.)) and various standards and/or protocols (e.g., cross-enterprise document sharing (XDS.A/B) cross-enterprise document media interchange (XDM) cross-enterprise document reliable interchange (XDR), patient identifier cross-referencing/patient demographics query (PIX/PDQ) patient administration management (PAM), query for existing data (QED), national counsel for prescription drug programs (NCPDP), etc.)) that makes system integration and/or communication more difficult. Thus, normalization may include reformatting of medical data to a consistent or compatible format for use within the MDD processing system 12. In an exemplary embodiment, the medical device data may be normalized into the ISO/IEEE 11073-10101 nomenclature and its extensions. In still further exemplary embodiment, the data quality management module 24 can normalize the streams of incoming time series data by converting units of measure. The data quality management module 24 can further operate to identify and tag various types of medical device data, locations from which the medical device data was received, or time series data streams originating from the same medical device. These tags can be used as further detailed herein to identify and analyze groups of streams of time series data.

In an exemplary embodiment, the data quality management module 24 normalizes the received incoming data by transforming and/or translating the clinical data streamed from the source healthcare system or device into a canonical data model with associated Metadata. The processed medical device data is stored in a data lake 26 which is exemplarily implemented in computer readable storage embodying capability to store terabytes of data. The data lake 26 is a long-term computer storage repository that holds large amounts of raw data in the its native format until the data is needed. The native format may include the time series data from the medical devices which may be in waveform or binary format, audio data, image data, and/or video data. In embodiments, this can help to facilitate the ingestion of the data that while may not be processed in real time, may still be taken in in real time or near real time and instead stored in the data lake until further needed. This may be facilitated by identifying particular data streams and limiting the processing of those data streams, for example by the data quality management module 24, if it is known at that time that such data stream is not being used in real time analysis. In an exemplary embodiment, the data quality management module 24 may not convert the data to a canonical data model but may still attempt to tag, enrich, or index the data to facilitate later retrieval of that data in a standardized way from the data lake 26.

In a still further embodiment, portions of the data that are stored in the data lake 26 may also be additionally stored in a graph database which may be a separate database residing on the same computer readable storage, or may be embodied on separate computer readable storage from the data lake. The graph database may receive the data streams of which it is known that the system may analyze trends in that data stream. The graph database may store the streams of data in a time series format in a way that facilitates trending of the date over time and appending the data with events either identified in the data itself, in one or more of the other data streams, or received by the system from an external source. These events may include, but are not limited to medical device or clinician actions, situations, or complications that arise during the medical procedure. The graph database may later be used by a clinician or technician to identify further relationships between trends and the data streams with other analysis as disclosed herein.

At the same time that the data is stored in the data lake 26, the enriched and normalized medical device data is provided to a stream processing engine 28 that uses artificial intelligence capability as described in further detail herein. The stream processing engine 28 identifies cases and events in the time series streams of medical device data. Identified clinical cases can be stored in an operational case database 30. Clinical cases may exemplarily include surgical and intensive care unit (ICU) cases. The clinical cases can be exemplarily identified by the medical device used and the timing of the medical data in the time series of the medical device data. For example, a time series of medical device data from an anesthesia delivery machine showing a change in status turning the machine and followed by changes to device settings and delivery and/or consumption of anesthetic agent all indicate that a clinical case has begun or is ongoing.

As noted above, the streams of time series medical device data originating from the same medical device or from the same location in a hospital may be tagged or otherwise identified as being related. These tags can be used to simultaneously analyze related data streams or combine analysis of related data streams to identify clinical cases. For example, a device status data stream analysis may be combined with a user input data stream, device setting data stream, and operational data streams to identify when the device is used and how it is used in the clinical case. This information may help to distinguish between a maintenance or checkout of the medical device by a technician from the use of the device for clinical case.

The analysis of the data streams of multiple medical devices, particularly those identified as being related or co-located can further be used to identify clinical cases. For example, coordinated or similar actions in data streams of an anesthesia delivery device and a related patient monitoring device, and/or respiratory and/or imaging device, etc. can further be used to identify that these devices are being used together for a clinical case. In still further embodiments, the streaming time series medical device data may be combined with information regarding scheduled clinical cases to help to further identify when and how the medical devices are used during clinical cases.

In embodiments, knowledge of a scheduled use of the medical device (e.g. anesthesia delivery machine) can be used to further identify clinical cases in the streams of medical device data. For example, input or received knowledge regarding a type and time of a scheduled procedure may help to identify the start and end of the clinical case in particular streams of medical device machine data. In an embodiment, a known schedule of use for the medical device can help to identify clinical cases from maintenance or calibration actions which may similarly require powering up and at least partial operation of the medical device.

The medical device data associated with the actions by the anesthesia delivery device and/or other medical devices during the identified clinical case are stored in the operational case database 30. In an example, the identification of the clinical case is stored along with the other time series streams of medical device data from that anesthesia delivery machine as well as time series streams of medical device data from any physiological monitors and/or other medical devices associated with the use of that anesthesia delivery machine. In another exemplary embodiment as described in further detail, a clinical case summary with links or identifiers to the associated time series medical device data stored in the data lake 26 can be created and stored in the operational case database 30.

In an embodiment, prior to storing the clinical cases in the clinical case database 30, the clinical cases may be classified or profiled which is a technique used for data curation. The profiling of the clinical cases may be based upon in part, the information in the clinical case summary, and as described in further detail herein, may be used to group the clinical cases into groups, for example normal cases, edge cases, and outlier cases. These determinations may be made in view of a comparison between the time series data in the clinical case against normal distributions of the same type of time series machine data in other similar clinical cases. Edge cases may be identified as borderline or ambiguous cases, not clearly defined as either normal or an outlier. In a merely exemplary embodiment, for a particular measured value or occurrence, a distribution of such occurrences may be used to establish normal, edge, and outlier cases. In a merely exemplary embodiment, a normal case may be within a standard deviation of a median value in the normal distribution while edge cases are between one and two standard deviations and outlier cases are greater than two standard deviations from the median. The categorized cases, as explained in further detail herein, for example, identified edge cases may be further investigated to create or improve event detection algorithms, rules for clinical decision support, alert algorithms, and predictive algorithms.

The stream processing engine 28 also identifies events in the time series streams of medical device data, for example in the manners as described in further detail herein and presented in business intelligence and visual analytics tools 32 which exemplarily may be presented on a graphical display communicatively connected to the medical device data processing system 12. The processing and reporting of events will be described in further detail herein with respect to FIG. 2.

Once clinical cases are stored in the operational case database 30, clinical cases can be reviewed manually by a clinician or technician using a curation and case review tool. The curation and case review tool 34 can be presented in a graphical user interface on a graphical display and further provide inputs exemplarily through the graphical user interface for the user or technician to curate or otherwise assess the clinical cases. This can be performed for investigative, educational, and data curation purposes. Exemplary and non-limiting embodiments of the data curation will be described in further detail herein with respect to FIG. 3.

The reporting and visual analytics tool 32 can present the detected events in a variety of channels of communication. Exemplarily as will be explained in further detail herein, and including, but not limited to, the detected events can be presented visually through graphical user interfaces and graphical displays. The detected events or notifications of the detected events can also be reported by communication of events/event notifications to wearable or mobile devices and presentation of medical device data and identified events in visual form in reports and/or dashboards presented in a graphical user interface on a graphical display.

The results of the streaming analytics and event detection in the time series of medical device data can be provided to an application programming interface (API) 38 for use by application developers to provide monitoring, reporting, and/or control applications based upon the analyzed streams of medical device data. Such applications may operate through a computer operating system, a website browser, or operate on a mobile computing device or wearable computing device. Non-limiting examples of applications that may leverage the analysis of the time series medical device data include, but are not limited to an anesthetic agent cost dashboard 40, a checkout dashboard 42, a supervisory application 44, an alarm management application 46, an asset management application 48, and a benchmarking application 50.

The agent cost dashboard 40, as will be explained in further detail herein with respect to FIG. 4, exemplarily presents medical device data regarding anesthetic agent use across clinical cases as well as between anesthesia delivery machines within a hospital network or comparatively between hospital networks. By comparatively presenting this information anesthetic agent use and behavioral changes can be understood and undertaken to promote efficient use of anesthetic agent.

The checkout dashboard 42, as will be explained in further detail with respect to FIG. 5, may exemplarily assist in monitoring the inspection and maintenance of the monitored medical devices. Medical device data such as device status and settings, as well as messages and information in machine data may provide insight into the inspection processes for maintaining medical devices at a hospital network. The checkout dashboard may identify maintenance and/or testing events in the streams of machine data and note these identified testing events against a testing schedule, requirement (e.g. daily), or other criterion.

A supervisory application 44 may be used by attending and/or supervising anesthesiologists to more efficiently manage remote personnel and/or nurse anesthetists simultaneously working across multiple locations or theatres. An alarm management 46 application can report and present medical device data regarding alarm notifications and silences of alarm notifications in order to better understand and adjust sheen alarms to improve signal to noise in alarm events and to reduce alarm fatigue by clinicians.

Asset management applications 48, as will be described in further detail herein with respect to FIG. 6, may present use, status, maintenance, and/or inspection information regarding medical devices (e.g. anesthesia delivery machines) or consumables used by medical devices, including components which while not replaced at every use must be frequently replaced, refilled, or refurbished during normal operation of the medical device (e.g. filters, absorbers). Benchmarking application 50 may provide further operational and quality performance across providers and/or organizations or in a comparative manner for example between hospital networks versus averages or between specific locations. Particular events and the application will be described in further detail herein.

Figure 2:
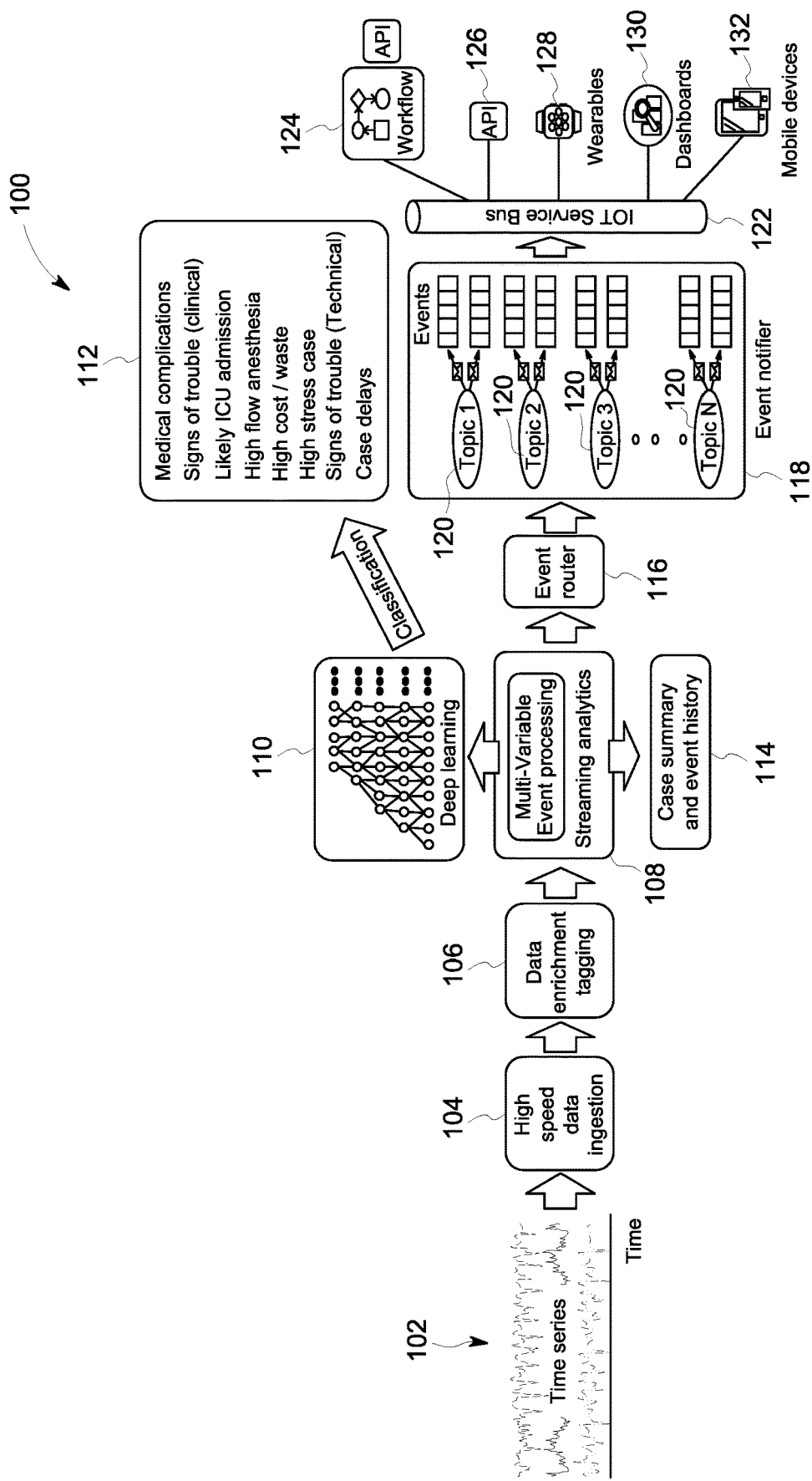
FIG. 2 depicts an exemplary embodiment of a method of medical device data processing.

FIG. 2 is a flow chart that depicts an exemplary embodiment of a method 100 of processing medical device data. In an exemplary embodiment the method 100 may be carried out by the medical device data processing system 12 as described above with respect to FIG. 1. As previously noted, embodiments of the systems and methods as described herein process medical device data as time series data of changes in each medical device data value 102. The data streams are acquired from the medical devices and may include time series format data regarding machine data such as alarms, device status, settings and values representing specific actions, messages, measured data. The medical device data may further include patient physiological data. At 104 the time series data streams, multiple streams from each medical device in a medical device network are ingested to prepare the incoming data for processing and/or saving. In one exemplary embodiment, the medical device data is machine data. At 106 the processed medical device data is enriched by tagging the streams of data with identifying information and/or converting units of incoming medical device data to normalize units. The data enrichment and tagging at 106 is performed without negatively impacting latency of the ingested streams of medical device data. Streaming analytics are undertaken at 108 with a clustered streaming analytics engine capable of complex event correlation, data smoothing, and windowing operations. The streaming analytics is exemplarily performed by predictive algorithms from deep learning as will be described herein and in further detail with respect to FIG. 3.

In streaming analytics data may be windowed into short segments against which the pattern recognition or predictive algorithms are applied. Further analysis can be applied between windowed portions of the time series and the windows overlap so that data is not missed and each segment of time series data is given both forward and backward context. As noted above, the analysis of the streaming time series data may not be limited to analysis of individual streams of data. Rather, different streaming analytics algorithms may relate the analysis of multiple streams of data, for example streams of data originating from the same medical device and/or streams of data originating from different medical devices but from the same location. This context may be provided by the tags added in the previous data enhancement. In still further embodiments, streaming analytics algorithms may analyze the streams of data in combination with other information as may be acquired from sources outside of the medical devices themselves. This other information may include but is not limited to time, date, hospital scheduling information or maintenance schedules in order to further carry out the clinical case identification and event detection as described herein.

The streaming analytic algorithms may exemplarily be alarm algorithms, control algorithms, event detection algorithms, or predictive algorithms. These algorithms may be predefined, or in other embodiments may be created as a result of automated learning, for example in the manners as described in further detail herein with respect to FIG. 3. Non-limiting examples of the streaming analytics algorithms may include early detection of deterioration of a patient's health status, detection of complications in an operating room (OR) or ICU, prediction of a medical device needing maintenance, prediction of complications in cases which may require future special care, or prediction of scheduled delays. In exemplary embodiments, the streams of machine data from the medical devices may reflect the manner in which the medical device is being used and from analysis of the operation of the medical device, an event such as a complication during a surgery may be detected based upon this machine data. As will be described in further detail herein, the prediction of such a delay can be leveraged to reorganize schedules or room assignments for later scheduled procedures. In still further embodiments, the streaming analytics algorithms can be used to predict a likelihood of admission to an intensive care unit from an operating room or to predict a likelihood of avoiding the ICU after a procedure in the OR. These predictions may exemplarily be based upon the manners in which the medical devices were used during the procedure in the OR as a result from analysis from the streaming machine data from these medical devices.

In still further exemplary embodiments, the streaming analytics algorithms may be used to detect deviations from standard practice and/or to detect cases completing ahead of schedule or with a delayed schedule. For example, these may be detected by an identification of an unusually long induction phase, maintenance phase, or emergent phase as determined from the operation of an anesthesia delivery machine as compared to normal or expected operation. In other exemplary embodiments the results of streaming analytics algorithms may be further be used to reduce nuisance alarms and to prioritize other alarms or patient critical alerts. Other exemplary embodiments apply streaming analytics algorithms to provide benchmarking of quality metrics for completion and provision of the procedures provided in the clinical case. Additionally, streaming analytics algorithms applied to the machine data of the medical device data can be used to infer likely activities and document the times at which activities occurs for procedure summary and reporting as well as to predict post procedure outcomes.

The streaming analytics at 108 may classify events detected in the time series medical device data. These identified events may be classified as reactive, predictive, or prescriptive. Reactive events are those events which have already occurred. Predictive events are the events with statistically ranked outcomes and prescriptive events are those predictive events which also include recommended actions. At 110 deep learning algorithms may further classify the events with more specificity than the above noted reactive, predictive, and prescriptive. In non-limiting examples, the deep learning algorithms may classify the events as medical complications, likely admissions to the ICU, adverse outcomes, operational delays, high cost/waste of medical resources, additional events may be classified which detect early signs of trouble which can be both clinical and technical in nature. Additionally, the detection algorithms may flag high stress cases in addition to identifying chronology of medical device use, including delivery of various anesthesia phases, machine checkout and maintenance events, or the prolonged practice of high flow anesthesia. As will be explained in further detail with respect to FIG. 3, the behavior and accuracy of the predictions improve over time with more data, patterns and through self learning.

Figure 3:
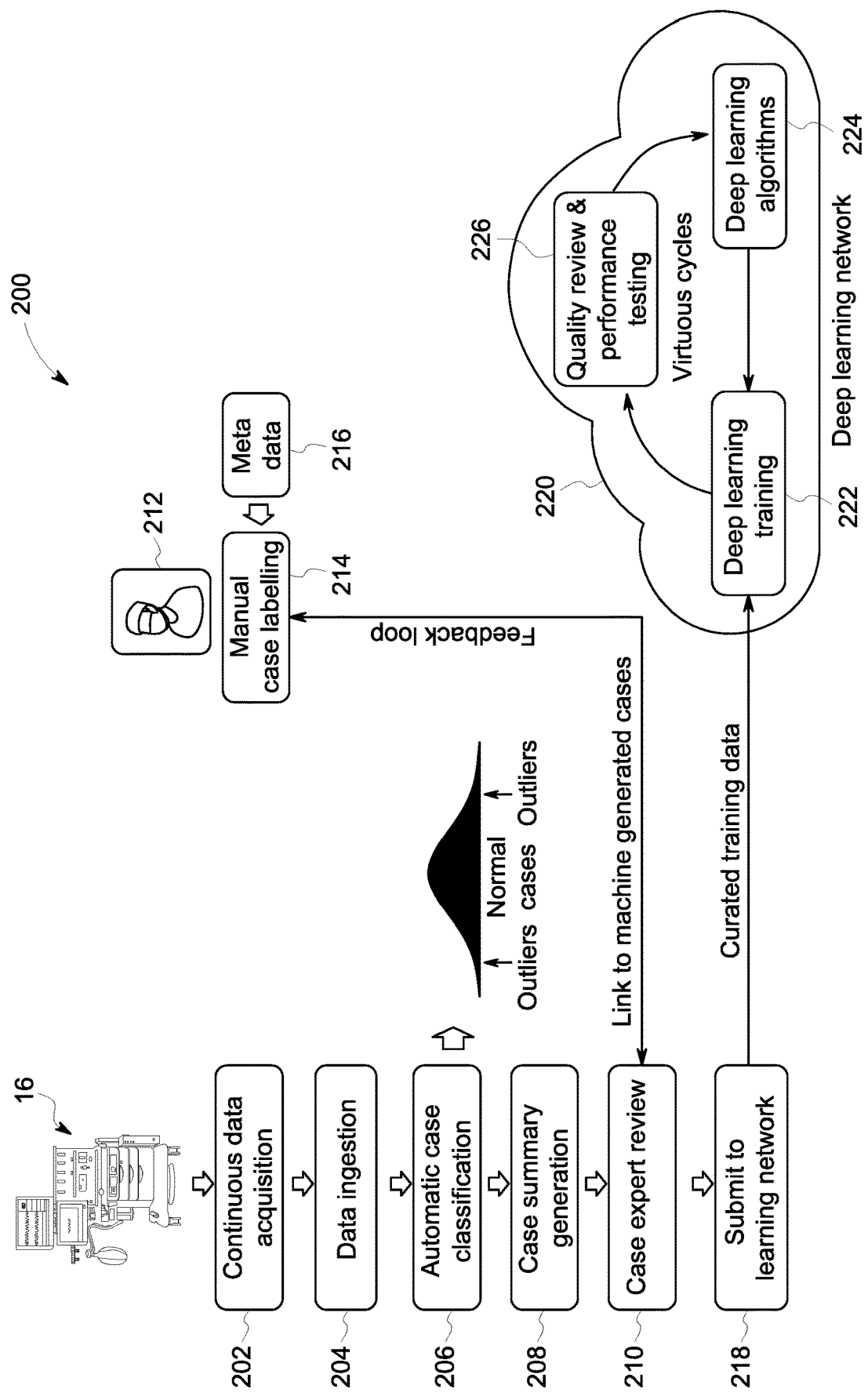
FIG. 3 depicts an exemplary embodiment of a method of medical device data curation and learning.

The deep learning at 110 can be used to produce algorithms 112 for example through the methods as described in further detail herein with respect to FIG. 3. These algorithms may in turn be used for streaming analytics. Non-limiting examples of algorithms which may be developed from the deep learning at 110, may include algorithms to detect medical complications, to detect signs of clinical trouble, predict likely ICU admission, detect high flow anesthesia, detect high anesthesia cost or ware, detect high stress cases, detect signs of technical trouble in the medical device, or predict delays in further scheduled cases in a unit based upon detected prior events.

A case summary module 114 maintains state information for the clinical cases and tracks associated events for particular clinical cases. The case summary module 114 further helps the streaming analytics 108 by identifying resent historical events to help the streaming analytics 108 from identifying the same events excessively in the time series data and further maintains identified events in the chronological order. For example, if a clinical case start has been identified, more focus can be placed on identifying a clinical case end.

In exemplary embodiments the streaming analytics at 108 can detect various events occurring in the streaming medical device data. Non-limiting examples of detected events may include those events which may be detected from a single data stream, for example a change in gas flow provided by an anesthesia delivery machine, for example a transition between high flow to low flow. An event that a machine checkout by a technician occurred may be detected, for example by noting a signal that is input or activated during a part of a checkout procedure. Various machine operability signals may be monitored, for example related to operation of a microprocessor to indicate whether or not the machine is with or without power or is in an on, off, or stand-by state. Respiratory events indicating patient airway troubles may be detected from the streaming machine data indicative of respiratory support provided to a patient in the cases of respiratory assistance for a spontaneously breathing patient or a clinician change to the respiratory support provided by a machine in the case of mechanical ventilation. Still further exemplary events which may be detected in the machine data include alarm status changes which indicate alerts and/or critical alarms, or technical alarms. In additional embodiments, events in the process of a medical procedure may be detected in the medical device machine data. For example, the start of a surgical case by detecting that medical devices are turned on or initialized, the detection of the start of the delivery of anesthesia or another medical device providing therapy or patient monitoring, detection of induction, maintenance or emergence phases, or the end of a medical procedure.

In still further exemplary embodiments, complex event processing may be used to identify events which occur upon event detection based not only upon the analyzed streaming medical device data, but also may be detected in view of the combination of multiple streams of medical device data and/or trends in various streams of medical device data.

Events detected by the streaming analytics at 108 are provided to an event router 116 which routes the identified events into predetermined groups or topics in an event notifier 118. The event notifier 118 receives the identified events from the event router into a plurality of groups or topics 120. The groups may be filled with similar events based upon type of medical procedure, type of device, location of device, or type of event. For example all of the events that are detected as originating from a particular hospital, or a particular OR may be grouped together for event notification. In another embodiment, all of the events related to a particular type of device e.g. an anesthesia delivery device, may be grouped together. In a still further example, any events detected related to anesthetic agent consumption may be grouped together. Within each group, the importance or severity of the events may be determined and a notification for the events produced accordingly. Low priority events may be stored to an event log for later review. While high priority events for example detected software or hardware malfunction, diagnostic or predictive events may be provided as disclosed herein to more directly alert responsible personnel.

A service bus 122 is connected to the event notifier and publishes the event notifications to the appropriate consuming endpoint depending upon the notification and the priority of the notification. Channels of transmission/communication of event notifications as well as personnel to which even notifications are communicated may be predetermined based upon the groups into which the event notifications are routed and/or services of the event notification. Notifications may be provided to workflow engines, for example as may be used to coordinate personnel and task workflow within a hospital at 124. Events may be directed to a push notification application programming interface (API) for sending and receiving push notifications to the identified recipient(s), for example on a wearable 128, a dashboard 130 on a laptop or desktop computer, or on a mobile device 132. In other embodiments, wearables, 128, dashboards 130, and/or mobile devices 132 may connect directly with the service bus 122, for example through an app or other program operating on the device that connects to the service bus 122.

FIG. 3 depicts an exemplary embodiment of a method 200 for data curation and deep learning. Exemplary embodiments of the method 200 may be carried out with the medical device data processing system 12 as described above with respect to FIG. 1. As depicted in FIG. 1 a plurality of medical devices 16 produce streaming time series of medical device data. The medical devices 16 may be located all within the same unit within a hospital, within the same hospital, or across a plurality of different hospitals and locations. The method 200 begins by continuously acquiring the streaming time series of medical device data at 202 from all of the medical devices. As noted above, the medical device data includes, but is not limited to data streams in time series format of machine data, for example alarms, device statuses, settings, messages, and data measured from device sensors. The medical device data may further include identified physiological data. These pluralities of streams of time series data from the plurality of medical devices are received by the medical device data processing system by ingesting the streams of data into the system to process the data for further processing and storage. At 206 the streaming analytics performed by the streaming processing engine 28 automatically detects clinical cases from the medical device data at 206. The clinical cases can be detected in the manners as described above. The identified clinical cases are further classified into normal cases and outlier cases. The identified clinical cases are saved, for example in the operational case database 30 and/or the data lake 26 with the summary of the case classification as normal or an outlier at 208. Edge cases and outlier cases are flagged at 210 for independent review by a clinician expert. The flagged cases are provided to clinician experts and are reviewed at 212 by the clinician expert. In the clinician expert review, the case summary of the identified clinical case is combined with the clinician's own manual case labeling at 214 and additional metadata 216 reviewed by the clinician in evaluating the flagged cases. The additional metadata reviewed at 216 may include the identified physiological information regarding the clinical case and/or events detected in that same clinical case. While at 218 the identified normal cases are submitted to the learning network at 220, the clinician expert has the option of submitting or withholding the reviewed edge or outlier cases from the learning network 220.

In a still further exemplary embodiment, identified clinical cases may further be evaluated and identified in a manner of case profiling. In exemplary embodiments, review and evaluation of clinical cases either automatedly or in a combination of clinician and automated review, can help to identify clinician work flows from the medical device data streams. For example, changes in anesthesia amounts during the course of a medical procedure can be identified and related to particular anesthesiologist techniques, work flows, or practices. For example, in one embodiment, anesthesiologist's use of anesthetic agent to control blood pressure may be identified while in other cases specific anesthesiologist's techniques or workflow, for example use of a "coasting maneuver" during an emergence phase may be detected.

Deep learning training 222 takes in new clinical cases and links the clinical cases and/or curated cases to the medical device data records in the data lake with each clinical case. The clinical cases and the associated medical device data are used by the deep learning network 220 to train deep learning algorithms 224. In embodiments, the deep learning network 22 may additionally incorporate curated data from a wide variety of clinical research institution that have joined into a shared learning and discovering community. The deep learning algorithms 224 may be predictive algorithms and/or rules which define particular outcomes, predicted outcomes or other events. The deep learning algorithms 224 are quality tested at 226 against the clinical cases and medical device data representing those clinical cases as stored in the data lake of the system. The deep learning algorithms 224 can be provided to the stream processing engine for use in the streaming analytics as previously described.

In a non-limiting embodiment, an anesthesia delivery management system 18 locally connected to a plurality of anesthesia delivery machines 16b at a hospital 14 receives the medical device data from each of the anesthesia delivery machines 16b. in an exemplary embodiment, the anesthesia delivery management system 18 may calculate a vapor flow rate for each anesthesia delivery machine 16b as it is used during an identified surgical case. This calculation may be based upon information obtained and identified from machine data from each of the anesthesia delivery machines 16b. A stream processing engine operating, for example, on the anesthesia delivery management system 18 can detect the event of a surgical case beginning through the anesthesia delivery machine data time series streams, for example which may show the anesthesia machine powering up going through an initial checkout process or cycle and then the initiation of delivery of anesthesia by the machine. This may be used by the stream processing engine to identify the clinical event of a surgery using anesthesia. Additional medical device data streams from that anesthesia delivery machine or other medical devices, e.g. a patient monitor, associated with that anesthesia delivery machine may also be used to identify the clinical event. The stream processing engine 28 may further receive a calculated anesthetic vapor flow rate from the anesthesia delivery management system 18, or may receive the individual device settings of the vaporizer to enable calculation of anesthetic vapor flow rate. Anesthetic vapor flow rate can be calculated based upon a fraction of inspired agent and the fresh gas flow rate. Still further embodiments may additionally require the expired minute volume the inspired minute volume and a fraction expired anesthetic agent.

Based upon the settings of the anesthesia delivery device, an anesthesia setting identifying the anesthetic agent delivered to the patient can be provided to the system. From the identified agent type, a conversion factor can be applied to the anesthetic vapor flow rate to arrive at the liquid anesthetic flow. Liquid anesthetic flow is used against the current volumetric cost of the liquid anesthetic agent. From this calculation, an instantaneous, average, or total anesthetic agent cost can be calculated.

FIG. 4 depicts an exemplary embodiment of an agent cost dashboard which may be presented as a GUI 400 on a graphical display which shows the comparative cost of the anesthetic agent use across a plurality of clinical cases. The dashboard presentation of comparative anesthetic agent use can be provided in a local system as described above, or if the medical device data processing system is implemented remotely via a cloud computing solution, the dashboard can be provided back to the hospital either to report the locally obtained data or data across a plurality of hospital locations rather than a local implementation.

In a still further exemplary embodiment, the medical device data processing system and methods as disclosed herein may be implemented and carried out locally rather than in a cloud-based implementation. In such an embodiment, for example the anesthetic agent use example described above may be carried out for example at the anesthesia delivery management system 18. An a non-limiting example of such an embodiment, the anesthesia delivery management system 18 may carry out the clinical case identification and event detection and notification processes as described above. The anesthesia delivery management system 18 may further perform the anesthetic agent cost analysis and reporting, exemplarily through a dashboard as depicted in FIG. 4. In a non-limiting exemplary embodiment, the streaming analytics may rely upon algorithms and/or rules supplied to the anesthesia delivery management system 18 rather than generated through a local deep learning process.

The agent cost dashboard GUI 400 exemplarily provides a variety of information across a plurality of anesthesia delivery machines. Exemplarily, temporal controls 402 enable the selection of analysis of daily or monthly data, and selection of the desired dates for review. The GUI 400 exemplarily depicts a review of monthly agent cost data. The GUI 400 reports monthly averages at 404, including both an average volume of anesthetic agent and an average cost of anesthetic agent both for introduction phase 406 and maintenance phase 408. In an exemplary embodiment, the maintenance phase is reported as an average cost per minute while the initiatoin phase is reported as an average cost per case. The GUI 400 further reports monthly totals at 410 including the number is machines considered in the report, the number of cases handled by those machines during the time period of the report, the volume of different anesthetic agent (e.g. sevoflurane, desflurane, and isoflurane) as well as the total cost of the anesthetic agent. Average consumption of anesthetic agents is reported at 412. This includes both a report as to the average volume of anesthetic agent consumed per case as well as a cost per minute of the various anesthetic agents used. The GUI 400 further reports the monthly totals of the anesthetic agent use, cases, and anesthetic agent cost in table 414. This table further includes a report of a daily trend versus a previous reference time period, for example a previously month of anesthetic agent use. The above noted average reports of anesthetic agent consumption and cost can be helpful in providing an overview of anesthetic agent use across an entire surgical unit, hospital, or hospital network. These average reports can help to identify general anesthetic agent use and cost trends which may help to guide anesthetic agent use and cost goals or practices in the future.

The GUI 400 further includes a more detailed machine report 416. The machine report identifies each of a plurality of anesthetic agent machines as monitored in the system (e.g. OR1-OR6). The machine report 416 presents information regarding the manner in which each device was specifically used, including, but not limited to the number of cases for which that machine was used in the report time period, the volume of various anesthetic agents used by operation of that machine, and the total cost of the anesthetic agent consumed during operation of each machine. The machine report further provides average anesthetic agent consumption during operation of the various machines. For example, it can be seen that across the exemplary 374 cases handled in the month of June 2016 by six different anesthesia delivery machines that all of the anesthesia delivery machines used roughly the same amount of anesthetic agent per minute during patient induction as reported at column 418. However, as reported in column 420 the average anesthetic agent consumed during maintenance varied far more significantly from a low of 1.6 L/min. during maintenance to a high of 2.1 L/min. during maintenance. This is a difference of nearly 25%. Such an identification in the machine report 416 may lead to further investigation of the use and/or operation of either the lowest consuming anesthesia delivery machine (OR1) or the highest consuming (in L/min.) anesthesia delivery machine (OR5) or both of these machines to determine whether these machines are used to handle different types of cases requiring more or less anesthetic agent or whether there are differences in the manners in which these two machines are used, helping to identify best practices and/or practices for remediation. In still further embodiments, as will be disclosed in further detail herein, such differences may help to indicate the need for machine maintenance or other actions.

FIG. 5 depicts an exemplary embodiment of an anesthesia delivery machine checkout dashboard exemplarily presented in GUI 500. Many medical devices, including complex therapeutic and/or diagnostic medical devices require frequent testing calibration, and/or other checkouts to ensure that the machine is operating correctly. The GUI 500 exemplarily presents visual indication as to when the required checkouts have occurred on each of the anesthesia delivery machines in the selected reporting unit. As noted above, detection of these checkout procedures can be obtained through analysis of the streaming machine data collected from the medical devices exemplarily anesthesia delivery machines. For example, the GUI 500 reports the status of six anesthesia delivery machines across four different checkout tests. These checkout tests include vent and gas 502, circuit leaks 504, low peaks 506, and agent delivery 508. Each of these tests may be a known automated or semi-automated routine carried out after initiation by a clinician or technician, or carried out in conjunction with inputs received by a clinician or technician. Therefore, for each of these checkout tests, the operation of the anesthesia delivery machine during the course of each test may be known. In one exemplary embodiment, particular operational characteristics may be added to a particular feature of the anesthesia delivery machine as would show up in one or more of the streams of machine data. For example, an identifiable function e.g. ramp function or step wise function in one or more of the streams of machine data may indicate the start of a particular test reported in the checkout dashboard. The system may further identify the initiation of a checkout test by a change in anesthesia delivery machine status for example to indicate a change to a testing mode or initiation of a particular test function. The GUI 500 further operates to report examples of successful and/or unsuccessful checkout tests, as well as an indication 510 if any checkout tests on any specific machines have not been performed within assigned or predetermined frequency.

Figure 6:
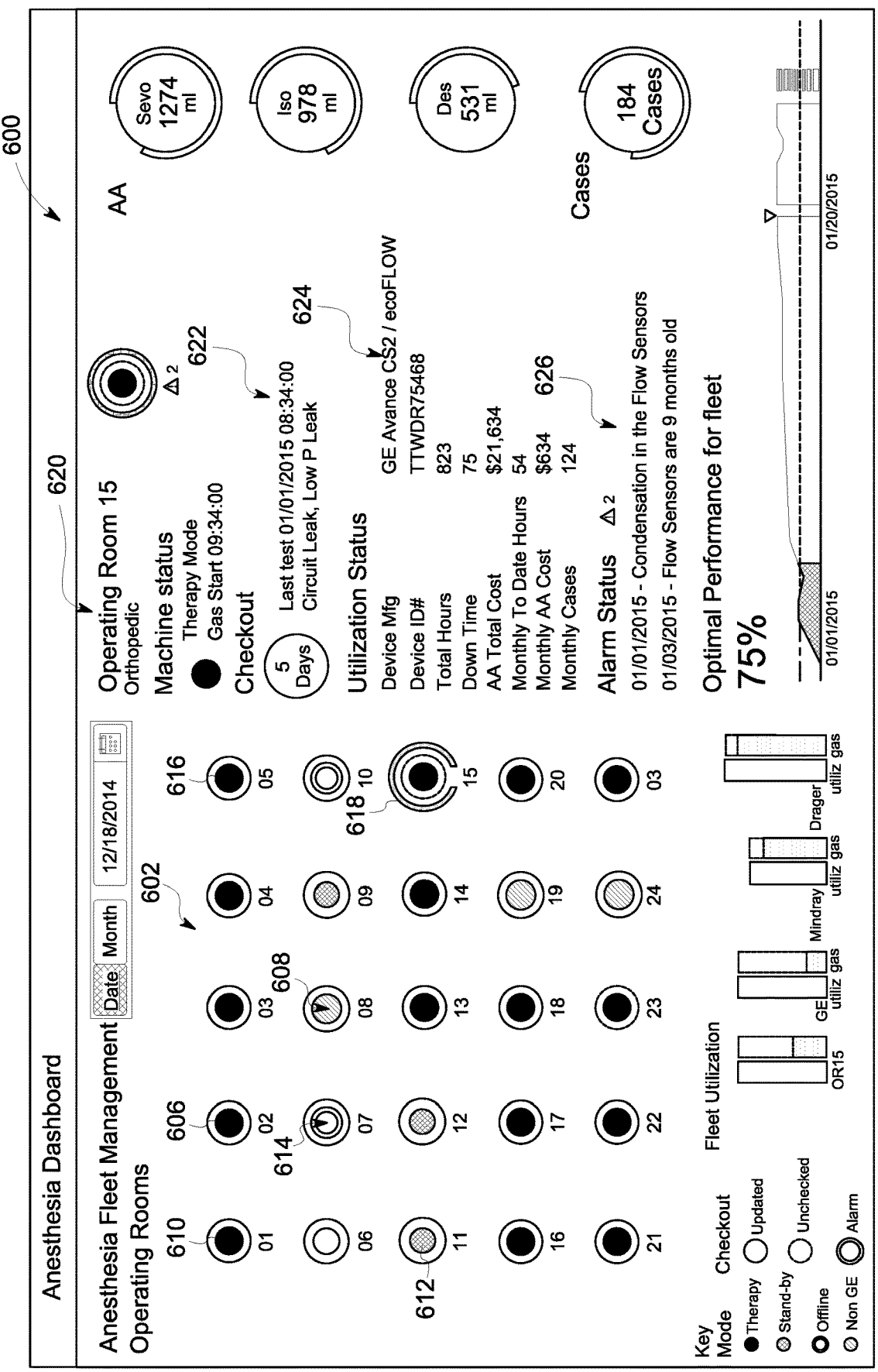
FIG. 6 depicts an exemplary embodiment of an asset management dashboard.

FIG. 6 depicts an exemplary embodiment of fleet management dashboard exemplarily in GUI 600. The exemplary embodiment of a fleet management dashboard exemplarily provides a large amount of information regarding anesthesia delivery machines across a fleet of devices for example in a surgical unit of a hospital. In an operating room summary 602, each anesthesia delivery machine located in each of 25 exemplary operating rooms is represented. A key 604 presents a graphical output of machine information and status whereby a center circle identifies a GE unit (solid color) 606 or a not-GE manufactured product as exemplarily indicated by hatched lines 608. The operational status of each of the anesthesia delivery machines is further indicated with e.g. green colored solid circle 610 indicating a anesthesia delivery machine in use to provide therapy while an e.g. orange colored solid circle 612 indicates an anesthesia delivery machine in a standby mode and an empty center circle 614 indicates an anesthesia delivery machine that is currently offline. Additional rings located around the center ring further indicate the checkout status as discussed above. Separate colors of intermediate rings 616 can indicate whether the anesthesia delivery machine has successfully passed the appropriate checkouts, requires checkout updating or has gone unchecked or has missed a scheduled checkout. Finally, an outer ring 618 can indicate alarm detected for each anesthesia delivery machine. It should be appreciated that other embodiments of the legend and coding may be envisioned and are within the scope of this disclosure. As noted above, this information can all be obtained through the data streams of machine data collected from the anesthesia delivery machines in the surgical unit. For example, the current operational status of each of the anesthesia delivery machines between offline, standby, or therapy modes can be determined from the streams of machine data as described above. Similarly, the checkout status can also be determined. In an embodiment wherein any alarm signals are provided in the machine data, the reported alarms status can be determined in this way as well.

Selection of any one of the anesthesia delivery machines in an exemplary operating room can pull up a detailed machine report 620. Exemplarily as found in FIG. 6 the machine report 620 can provide a current machine status indicating the mode in which the anesthesia delivery machine is currently operating, and also an indication of when the anesthesia delivery machine last changed status. A checkout report 622 provides a summary of information as may have so been presented in a checkout dashboard, indicating a checkout status, need for checkout test, and/or a result of a most recent checkout test.

A device utilization status 624 reports both identifying information regarding the particular anesthesia delivery machine as well as reports regarding the machine use. Information regarding machine use can be kept track of by analysis of the streams of machine data to identify total hours of use in a therapy mode, total hours in a standby mode, and utilization regarding numbers of case and anesthetic agent delivered with the machine. In still further exemplary embodiments, some medical devices may be operated in different therapeutic modes. In a non-limiting embodiment, some anesthesia delivery machines may be optionally operated at a mechanical ventilator without delivery of anesthetic agent. A utilization status 624 may further breakdown in the modes of use of that particular medical device. For example, this may be detected in a comparative manner based upon the streams of machine data related to both anesthetic agent delivery and the provision of respiratory support. Detection of operation of a machine to provide respiratory support without the delivery of anesthetic agent can be an indication that the medical device is being used to provide only respiratory support while in other uses, the same machine may be used to only deliver anesthetic agent or to deliver both anesthetic agent and respiratory support. In still further exemplary embodiments, a machine status provided in a stream of machine data from the anesthesia delivery machine may indicate whether the machine is operating in a anesthesia delivery, respiratory support, or combinational function. In an example, this information may also be provided to the business intelligence and visual analytics tools 32 as previously described to present insight into a clinical use and operation of medical devices.

An alarm status 616 can provide a more detailed explanation of the detected alarms. These detected alarms may exemplarily be technical alarms, for example detection of condensation on the flow sensors, or an excessive age of flow sensors as indicated in the example of FIG. 6, although the alarms are not herein so limited to only technical alarms.

Figure 7:
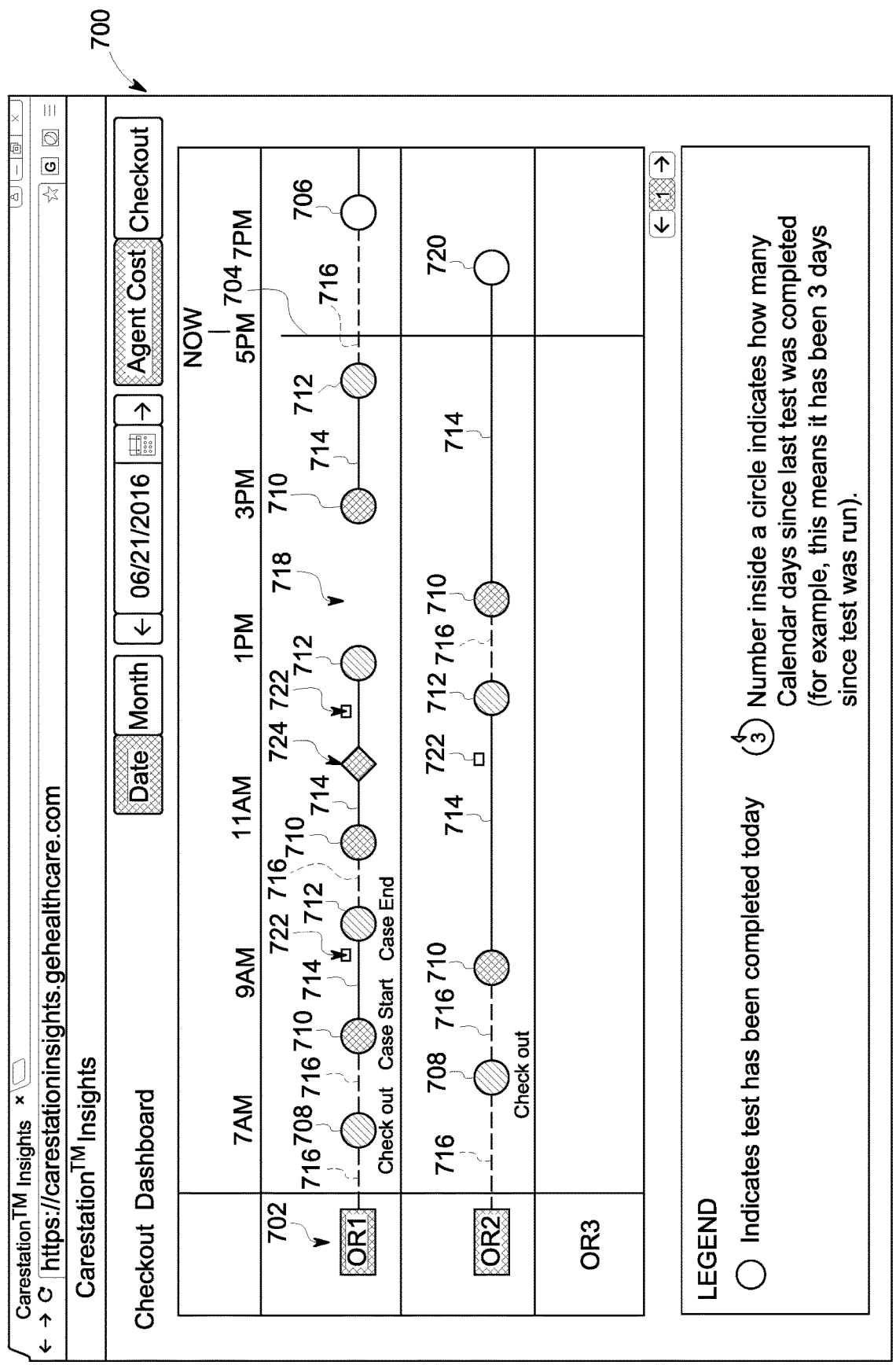
FIG. 7 depicts an exemplary embodiment of a checkout dashboard.

FIG. 7 depicts a further exemplary embodiment of an operational dashboard presented as GUI 700. In the GUI 700, a temporal view of the use each of a plurality of operating rooms 702 is reported to visualize both a current status of the use of an operating room, but also a future schedule of the operating room, this visualization can assist a clinician or clinical manager in staffing and/or scheduling management to estimate and/or reflect whether the operating room use is on time or behind schedule. In an event that actual performance of the clinical procedures are deviating from the schedule, accommodations may be made to move future procedures to another room or with alternative accommodations.

The GUI 700 exemplarily presents a temporal presentation with a line 704 indicating a current time. Future scheduled events 706 are presented to the right of the line 704 while the actual timing of the procedures as they occurred are presented to the left. The events of the procedures as they occurred can be detected by analysis of one or more streams of medical device data, including streams of machine data from multiple medical devices located in each of the operating rooms 702. The analysis of machine data from multiple medical devices associated with a medical procedure can further improve accuracy of event detection by the correlated indications found in the machine data of these separate devices. In an exemplary embodiment, individual circles may indicate checkout procedures 708 while connected circles indicate the start 710 and ends 712 of various procedures. The operational status of machines or events may be indicated by a line. Exemplarily solid lines 714 indicate an active procedure while dashed lines 716 indicate a standby status. A gap or no line 718 may indicate when machines are off or a facility is otherwise closed. In an exemplary embodiment, when a procedure is currently ongoing, the system may produce an estimation 720 of a procedure end time. This estimation of procedure end time 720 may be exemplarily based upon the underlying schedule as well as any detected events in the medical device data during the procedure thus far that would indicate a delay in the estimated procedure end time. Detected events 722 may be indicated along the procedure which may indicate a prolonged procedure. Still further events, for example a secondary induction phase 724 may be indicated as such an event may further indicate a prolonged procedure. In exemplary embodiments, medical devices may be designed to incorporate additional sensors such as to further collect and report machine data as used in exemplary embodiments described herein. Such machine data may exemplary include flow sensors or valve cycles, processor clock speeds, component voltages. Changes in these signals may exemplarily be used to track a condition and/or "wearing out" of consumables and/or commonly replaced components of a medical device, non-limiting exemplary embodiments may include a $CO_2$ absorber, humidifier, filters, valves, or gas sensors.

In exemplary embodiments, analysis of machine operational status (e.g. in use, standby status, and offline) may further provide information and insights not only to a hospital to assist in efficient management of medical device assets, but may further provide generalized information regarding specific use case and use trends to provide insight into field use of medical devices, in still further exemplary embodiments, maintenance, use, or other schedules may be based upon utilization reports specific to particular devices.

In a still further exemplary embodiment, the analysis of the streams of medical device data may further facilitate clinical record keeping and report management for a particular medical procedure. In an exemplary embodiment, analysis of the anesthesia delivery machine data can yield a summary report that indicates time of use, duration of use, anesthetic agent delivered, as well as a log of anesthesia delivery events, inputs, or changes in the anesthesia delivery. As this information can be detected in the streams of medical device data, such a report and/or summary can be automatedly produced and electronically provided to a clinician for review and approval and/or revision and the annotation with additional comments. In an exemplary embodiment, the detected events and/or anesthetic agent use in the procedure may be associated to medical billing codes and a provisional medical billing report provided to the clinician or another hospital personnel for review and billing submission. In an exemplary embodiment, the electronic case summary report may be expressed in the HL7 clinical document architecture standard for example to be incorporated into a patient's electronic medical record and/or to facilitate use for billing documentation.

In an exemplary embodiment, the streaming analytics of the time series medical device data can include a combined analysis of machine data and physiological data related to the same patient in real time or near real time. Upon evaluation of this combined information the patient condition and current device settings and operation can be determined. Based upon this determination, particular events may be identified, these events being recommended changed to medical device settings or parameters. This may include adjustments to any of the values in the received machine data or other identified medical device settings, including alarm parameters. In one exemplary embodiment, these events results in notifications to a responsible clinician with recommendation for such medical device setting changes. In other exemplary embodiments, the medical device data processing system communicates back to the medical devices, for example through the gateway 20 to provide operational instructions and/or medical device setting adjustments directly to the medical device. In a still further exemplary embodiment, such recommended actions may first be presented to a clinical or technician for approval and/or confirmation prior to the MDD processing system providing such instructions directly to one or more medical devices.

Exemplary embodiments of the systems and methods as described herein gather machine data produced by a plurality of medical devices in real time and at a high frequency approaching the frequency at which such machine data is produced by the medical devices. Streaming analytics of this machine data can yield large amounts of machine use and medical procedure data that, in exemplary embodiments is, by its nature de-identified. This procedure data can be summarized for improved retrieval and access at a later date, but stored in its raw form for use in data analytics and machine learning to automatedly produce are and improved algorithms exemplarily for use in the streaming analytics of the medical device data.

Embodiments of the systems and methods as described herein improve upon existing health information systems/electronic health records data as that data is typically focused on patient physiological data and reported and/or recorded at longer time intervals. The low frequency of this data limits the types of clinical decision support that can results from these sources of data. For example reduced data resolution can lead to inaccuracy in detection of minimum and maximum values and transient events/values in the collected data. Furthermore, the use of patient physiological data introduces concerns and/or challenges of maintaining such information in a confidential and/or de-identified state.

In the above description, certain terms have been used for brevity, clarity, and understanding. No unnecessary limitations are to be inferred therefrom beyond the requirement of the prior art because such terms are used for descriptive purposes and are intended to be broadly construed. The different systems and method steps described herein may be used alone or in combination with other systems and methods. It is to be expected that various equivalents, alternatives and modifications are possible within the scope of the appended claims.

The functional block diagrams, operational sequences, and flow diagrams provided in the Figures are representative of exemplary architectures, environments, and methodologies for performing novel aspects of the disclosure. While, for purposes of simplicity of explanation, the methodologies included herein may be in the form of a functional diagram, operational sequence, or flow diagram, and may be described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology can alternatively be represented as a series of interrelated states or events, such as in a state diagram. Moreover, not all acts illustrated in a methodology may be required for a novel implementation.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system for processing medical device data, the system comprising:
  at least one computer memory to store computer-executable instructions; and
  a processor to execute the computer-executable instructions, wherein the computer-executable instructions cause the processor to:
    receive a plurality of streaming time series of medical device data from one or more medical devices in real time or near real time, wherein the medical device data comprises machine data comprising at least one alarm, at least one device status, at least one device setting, at least one message, or a combination thereof;
    store the plurality of streaming time series of medical device data in the at least one computer memory;
    apply a plurality of case identification rules to the plurality of streaming time series of medical device data to identify portions of the plurality of streaming time series of medical device data representing clinical cases in the plurality of streaming time series of medical device data, wherein the portions of the plurality of streaming time series representing the clinical cases are identified based on a change in a status detected by delivery or consumption of an anesthetic agent, wherein the plurality of streaming time series of medical device data comprises binary data;
    execute streaming analytics to apply a plurality of event detection rules to the portions of the plurality streaming time series of medical device data corresponding to the identified clinical cases to identify events within the streaming time series of medical device data of each identified clinical case;
    generate one or more groups for the identified events based upon predefined recipients of notifications for the identified events;
    transmit an event notification for each of the identified events to the predefined recipients associated with the one or more groups across at least one communication platform associated with the one or more groups, the event notification indicating a change to an alarm parameter of the one or more medical devices, wherein the change to the alarm parameter is applied to the one or more medical devices automatically by the system; and
    automatedly refine at least one case identification rule or at least one event detection rule with the plurality of stored clinical cases in a learning network.

2. The system of claim 1, wherein the portions of the plurality of streaming time series of the medical device data representing the clinical cases are further identified based on a start of a surgical case, a start of a medical device providing therapy or patient monitoring, detection of induction, maintenance or emergence phases, or an end of a medical procedure, or a combination thereof.

3. The system of claim 1, wherein the processor is to preprocess the streaming time series of medical device data, wherein the streaming time series of medical device data comprises raw sensor data.

4. The system of claim 1, wherein the processor is to process the streaming time series of medical device data to provide the time series of medical device data in one or more consistent units of measurement.

5. The system of claim 4, wherein the processor is to create a clinical case summary from the streaming time series medical device data and store the clinical case summary in a clinical summary database, wherein each clinical case summary stored in the clinical case summary database is linked to the portions of the plurality of streaming time series of medical device data associated with the identified clinical case resulting in the clinical case summary.

6. A method for medical device data processing, the method comprising:
  receiving, in real time or near real time, a plurality of streaming time series of medical device data from one or more medical devices, wherein the medical device data comprises machine data comprising at least one alarm, at least one device status, at least one device setting, at least one message, or a combination thereof;
  storing the plurality of streaming time series of medical device data in at least one computer memory;
  applying a plurality of case identification rules to the plurality of streaming time series of medical device data to identify portions of the plurality of streaming time series of medical device data representing clinical cases in the plurality of streaming time series of medical device data, wherein the portions of the plurality of streaming time series representing the clinical cases are identified based on a change in a status detected by detecting delivery or consumption of an anesthetic agent;
  upon identification of a clinical case in the streaming time series medical device data, storing the portions of the plurality of streaming time series of medical device data of the identified clinical cases in a computer memory;
  conducting further streaming analytics to apply a plurality of event detection rules to the portions of the plurality streaming time series of medical device data corresponding to the identified clinical cases to identify events within the streaming time series of medical device data of each identified clinical case; and
  generating one or more groups for the identified events based upon predefined recipients of notifications for the identified events;
  transmitting an event notification for each of the identified events to the predefined recipients associated with the one or more groups across at least one communication platform associated with the one or more groups, the event notification indicating a change to an alarm parameter of the one or more medical devices, wherein the change to the alarm parameter is applied to the one or more medical devices automatically by the system; and
  automatedly refining at least one case identification rule or at least one event detection rule with the plurality of stored clinical cases in a learning network.

7. The method of claim 6, wherein the portions of the plurality of streaming time series of the medical device data are further identified based on a start of a surgical case, a detection of a start of delivery of anesthesia or a medical device providing therapy or patient monitoring, detection of induction, maintenance or emergence phases, an end of a medical procedure, or a combination thereof.

8. The method of claim 6, wherein the medical device data comprises machine data, wherein the machine data comprises at least one alarm, at least one device status, at least one device setting, at least one message, or a combination thereof.

9. The method of claim 6, further comprising:
evaluating stored clinical cases as normal cases or outlier cases; and
providing the outlier cases to a user for manual review.

10. The method of claim 9, further comprising tagging outlier cases with outcome data to facilitate manual review by the user.

11. The method of claim 10, further comprising receiving an input of an acceptance by the user regarding an outlier case of the plurality of outlier cases and upon the input of the acceptance, providing the outlier case to a learning network.

12. The method of claim 11, further comprising:
providing the normal cases to a learning network comprising a plurality of stored clinical cases.

13. The method of claim 6, wherein the one or more medical devices include at least one anesthesia delivery machine, and wherein the streaming time series of medical device data comprises streaming time series data of anesthetic agent use.

14. The method of claim 13, further comprising receiving surgical event scheduling data and wherein the streaming analytics further comprises applying the surgical event scheduling data to the streaming time series data of anesthetic agent use to identify a start and an end for each of the identified clinical cases.

15. The method of claim 13, further comprising: providing an anesthetic agent use dashboard on a graphical display, the anesthetic agent use dashboard to comparatively present the anesthetic agent used by the at least one anesthesia delivery machine across a plurality of clinical cases comprising the administration of anesthesia.

16. The method of claim 13, further comprising normalizing the streaming time series data of anesthetic agent use by converting the time series data of anesthetic agent use to time series data of liquid anesthetic flow.

17. The method of claim 6, further comprising evaluating stored clinical cases from the computer memory to profile clinician actions in the operation of the one or more medical devices.

18. A non-transitory machine-executable medium for processing medical device data, the non-transitory machine-executable medium comprising a plurality of instructions that, in response to execution by a processor, cause the processor to:
receive a plurality of streaming time series of medical device data from one or more medical devices in real time or near real time, wherein the medical device data comprises machine data comprising at least one alarm, at least one device status, at least one device setting, at least one message, or a combination thereof;
store the plurality of streaming time series of medical device data in the at least one computer memory;
apply a plurality of case identification rules to the plurality of streaming time series of medical device data to identify portions of the plurality of streaming time series of medical device data representing clinical cases in the plurality of streaming time series of medical device data, wherein the portions of the plurality of streaming time series representing the clinical cases are identified based on a change in a status detected by delivery or consumption of an anesthetic agent, wherein the plurality of streaming time series of medical device data comprises binary data;
execute streaming analytics to apply a plurality of event detection rules to the portions of the plurality streaming time series of medical device data corresponding to the identified clinical cases to identify events within the streaming time series of medical device data of each identified clinical case;
generate one or more groups for the identified events based upon predefined recipients of notifications for the identified events;
transmit an event notification for each of the identified events to the predefined recipients associated with the one or more groups across at least one communication platform associated with the one or more groups, the event notification indicating a change to an alarm parameter of the one or more medical devices, wherein the change to the alarm parameter is applied to the one or more medical devices automatically by the processor; and
automatedly refine at least one case identification rule or at least one event detection rule with the plurality of stored clinical cases in a learning network.

19. The non-transitory machine-executable medium of claim 18, wherein the portions of the plurality of streaming time series of the medical device data are further identified based on a start of a surgical case, a detection of a start of delivery of anesthesia or a medical device providing therapy or patient monitoring, detection of induction, maintenance or emergence phases, an end of a medical procedure, or a combination thereof.

20. The system of claim 1, wherein the plurality of streaming time series of medical device data further comprises a plurality of waveforms and numeric data in a time series format.

* * * * *